(12) United States Patent
Baba (10) Patent No.: US 8,106,012 B2
(45) Date of Patent: Jan. 31, 2012

(54) METHODS FOR PREDICTING EFFECTIVENESS OF APHERESIS THERAPY FOR HEART FAILURE

(75) Inventor: Akiyasu Baba, Tokyo (JP)

(73) Assignee: The Kitasato Institute, Tokyo (JP)

( * ) Notice: Subject to any disclaimer, the term of this patent is extended or adjusted under 35 U.S.C. 154(b) by 393 days.

(21) Appl. No.: 12/413,968

(22) Filed: Mar. 30, 2009

(65) Prior Publication Data

US 2010/0055038 A1    Mar. 4, 2010

(30) Foreign Application Priority Data

Aug. 27, 2008  (JP) ................................ 2008-218033

(51) Int. Cl.
*A61K 38/00* (2006.01)
(52) U.S. Cl. ........................................ 514/16.4; 607/17
(58) Field of Classification Search ................. 514/16.4; 607/17
See application file for complete search history.

(56) References Cited

OTHER PUBLICATIONS

Baba, Akiyasu, "Autoantigen Estimation and Simple Screening Assay Against Cardiodepressant Autoantibodies in Patients with Dilated Cardiomyopathy", Therapeutic Apheresis and Dialysis, vol. 12. No. 2, 2008, pp. 109-116.

Baba, Akiyasu, "Respiration and Circulation", Apr. 15, 2008; 56(4):371.5 and English Translation, pp. 1-10.

Felix, Stephan B. (MD) et al, "Removal of Cardiodepressant Antibodies in Dilated Cardiomyopathy by Immunoadsorption", Journal of the American College of Cardiology, vol. 39, No. 4, Feb. 20, 2002, pp. 648-652.

Staudt, Alexander (MD) et al, "Potential Role of Humoral Immunity in Cardiac Dysfunction of Patients Suffering from Dilated Cardiomyopathy", Journal of the American College of Cardiology. vol. 44, No. 4, Aug. 18, 2004, pp. 829-836.

*Primary Examiner* — Ralph Gitomer
(74) *Attorney, Agent, or Firm* — Andrus, Sceales, Starke & Sawall, LLP (57) ABSTRACT

The present invention provides methods for predicting an effectiveness of apheresis therapy on patients with dilated cardiomyopathy, which include adding, for example, sera or such collected from patients to 18-day-old chicken fertile eggs and measuring the left ventricular ejection fraction of the eggs. High reproducibility was achieved by using urethane as an anesthetic agent for the chicken fertile eggs, maintaining the eggs in incubation sand at 40° C. during measurement, and using an ultrasonic probe with a frequency of 10 MHz or more. When the left ventricular ejection fraction is less than 90%, apheresis therapy is likely to be effective. Indeed, it has been clinically demonstrated that the apheresis therapy is successful when the left ventricular ejection fraction is improved to 90% or more by the therapy.

8 Claims, 6 Drawing Sheets

METHODS FOR PREDICTING EFFECTIVENESS OF APHERESIS THERAPY FOR HEART FAILURE

FIELD OF THE INVENTION

The present invention relates to methods for predicting the therapeutic effectiveness of apheresis therapy in the treatment of dilated cardiomyopathy.

BACKGROUND OF THE INVENTION

Apheresis therapy is a treatment method that removes autoantibodies from peripheral blood via extracorporeal circulation to control autoimmune disorders and improve pathological conditions. Apheresis therapy has already been performed to treat dilated cardiomyopathy in the United States (U.S.) and Europe, particularly in Germany. However, the effectiveness of apheresis therapy reportedly varies depending on the case. Thus, it has been attempted to predict the effectiveness prior to treatment using cultured rat cardiomyocytes (Staudt A. et al., J Am Coll Cardiol. 44(4): 829-836, 2004).

In these attempts, however, the preparation of cultured rat cardiomyocytes has been technically complicated, and the cost effectiveness and reproducibility have also been problematic. The assay method using chicken fertile eggs, an alternative to the above method, has not been performed for predicting therapeutic effectiveness.

SUMMARY OF THE INVENTION

An objective of the present invention is to provide methods for predicting the effectiveness of apheresis therapy in the treatment of dilated cardiomyopathy.

If clinically convenient prediction of the effectiveness of apheresis therapy is established, it will enable an efficient treatment. The present inventors succeeded in developing such a simple screening assay system during a study aimed at elucidating autoimmune disorders in Japanese patients with dilated cardiomyopathy.

Specifically, through clinical trials on apheresis therapy for dilated cardiomyopathy patients in Japan (University hospital Medical Information Network (UMIN), Clinical Trials Registry (CTR), No. 623), the present inventors discovered that a simple screening assay system using chicken fertile eggs could be used as a method for predicting the therapeutic effectiveness. The present inventors also discovered that the assay system was cost effective, simple to operate, and highly reproducible.

Specifically, the methods comprise adding test samples (patient's serum, plasma, purified immunoglobulin, or such) collected from dilated cardiomyopathy patients to chicken fertile eggs, and measuring chicken left ventricular ejection fraction by echocardiography.

The present invention relates to methods for predicting the effectiveness of apheresis therapy in the treatment of dilated cardiomyopathy. Specifically, the present invention provides:
(1) a method for predicting the effectiveness of apheresis therapy on a patient with dilated cardiomyopathy, comprising the steps of:
 (a) adding a test sample obtained from said patient to a chicken fertile egg;
 (b) measuring left ventricular ejection fraction (LVEF) of said chicken fertile egg; and
 (c) predicting that apheresis therapy may be effective for the patient when said LVEF is reduced by the addition of said test sample;
(2) the method of (1), wherein the test sample is serum, plasma, or purified immunoglobulin;
(3) the method of (1), wherein the chicken fertile egg is 18 days old;
(4) the method of (1), wherein the chicken fertile egg is incubated at 40° C. during the measurement in step (b);
(5) the method of (1), wherein LVEF is measured by ultrasonic echocardiography;
(6) the method of (5), wherein ultrasonic probe frequency is 10 MHz or higher in step (b);
(7) the method of (1), which comprises the step of administering an anesthetic agent to the chicken fertile egg before step (b); and
(8) the method of (7), wherein the anesthetic agent is urethane.

BRIEF DESCRIPTION OF THE DRAWINGS

FIG. 1 is a set of photographs showing ultrasonic echocardiography (UCG) examination to determine the effects of autoantibodies on cardiac function in chick embryo hearts. Important snapshots are summarized in turn from the left. Initially, a small hole is made in each egg in order to add an anesthetic agent and patient IgG. Then, for UCG to be performed, the eggs were placed in warmed sand, and wider holes were made for the UCG probe. Finally, the M-mode was recorded to measure the left ventricular ejection fraction.

FIG. 2 shows detection of cardiodepressant autoantibodies in the chick embryo hearts. The left ventricular ejection fraction was measured by echocardiography after adding purified IgG (N=114) or saline (N=10). Cardiodepressant autoantibodies were found to be positive in 65 patients with DCM (DCM+), but negative in the remaining 39 patients with DCM (DCM−). The cardiac function remained unchanged even after adding IgG purified from non-DCM patients with heart failure (N=10).

FIG. 5-1 is a schematic diagram showing the manner of adding an anesthetic agent and patient serum into a chicken fertile egg. 1: incubator (37.8° C. air); 2: 18-day-old chick (in egg); 3: injector.

FIG. 5-2 is a schematic diagram showing the manner of echocardiography of a chicken fertile egg. 1: incubator (40° C. sand); 2: 18-day-old chick (in egg); 3: ultrasonic echocardiography probe.

FIG. 5-3 is an M-mode echocardiographic image of a chicken fertile egg (measurement of the left ventricular ejection fraction). 1: left ventricular end-systolic dimension; 2: left ventricular end-diastolic dimension.

DETAILED DESCRIPTION OF THE INVENTION

The present invention provides methods for predicting the effectiveness of apheresis therapy for dilated cardiomyopathy.

In a preferred embodiment of the present invention, the prediction methods comprise adding to chicken fertile eggs samples (test samples) obtained (collected) from dilated cardiomyopathy patients and predicting the probability of success in the apheresis therapy based on the left ventricular ejection fraction (LVEF) of the fertile eggs.

In the methods of the present invention, samples collected from patients (which may be herein referred to as "patient samples") include, for example, sera, plasma, and purified immunoglobulin. When sera or plasma are used as patient samples in the present invention, the amount of sample added to chicken fertile eggs is, for example, 50 to 400 µl, preferably 100 to 300 µl, and more preferably 200 µl. When purified immunoglobulin is used as a patient sample, the amount added to chicken fertile eggs is, for example, 0.2 to 3 mg, preferably 0.5 to 2 mg, and more preferably 1 mg.

The chicken fertile eggs used in the methods of the present invention are not particularly limited as long as heart function is developed. Such eggs are, for example, 15 days old or older, preferably 17 days old or older, and more preferably 18 days old or older.

In the present invention, patient samples are added to chicken fertile eggs. More specifically, the samples are preferably administered to the air sac of eggs.

The methods of the present invention comprise adding test samples (patient samples) obtained from dilated cardiomyopathy patients to chicken fertile eggs, and measuring LVEF of the chicken eggs.

In the present invention, LVEF can be measured by those skilled in the art using known methods. For example, LVEF can be appropriately measured by echocardiography.

When LVEF of chicken fertile eggs is measured, the frequency of the ultrasonic probe is preferably set at 10 MHz or higher, and the condition for incubating chicken fertile eggs is, for example, 38° C. to 42° C., preferably 39° C. to 41° C., and more preferably 40° C. More specifically, an example of the condition is 40° C. in warmed sand.

In a preferred embodiment of the present invention, when the measured chicken LVEF is lower than the "mean−2×standard deviation (%)" of that measured in the absence of the patient sample, it is predicted that apheresis therapy may be successful in the patient. In other words, it is determined that apheresis therapy would likely be effective for the patient. Specifically, when the condition for incubating chicken fertile eggs is 40° C., a chicken LVEF of lower than 90% gives the above prediction.

Whether apheresis therapy was successful or not can be determined as follows. For example, when LVEF in the above-described chicken fertile eggs after apheresis therapy is equal or higher than the "mean−2×standard deviation (%)" of that measured in the absence of the patient sample, it is determined that the apheresis therapy in the patient was successful.

Before measuring LVEF of chicken fertile eggs, an anesthetic agent is preferably administered to the eggs. Anesthetic agents used in the methods of the present invention include, for example, urethane, and the mixture of urethane and α-chloralose. When urethane is used as an anesthetic agent, it is preferably administered at 40 to 50 mg/egg.

In a preferred specific embodiment, the methods of the present invention include, for example, the steps of:
(a) adding a serum collected from a patient to chicken fertile eggs;
(b) measuring the left ventricular ejection fraction (LVEF) of the chicken fertile eggs; and
(c) predicting (determining) that the apheresis therapy may be successful in the patient when the left ventricular ejection fraction is less than the "mean−2×standard deviation (%)" of that measured in the absence of the serum.

The present invention enables pre-treatment selection of patients who are expected to receive a therapeutic effect by apheresis therapy for dilated cardiomyopathy. This can eliminate waste of expensive medical devices, and thereby reduce patients' burden of medical expenses. Furthermore, the present invention allows ready comprehension of patients' conditions under which the apheresis therapy is effective, and is therefore advantageous in that appropriate timing of apheresis therapy can be determined.

All prior art references cited in this specification are incorporated herein by reference.

EXAMPLES

Hereinbelow, the present invention will be specifically described with reference to Examples, but the technical scope of the present invention is not to be construed as being limited thereto.

Example 1

Identification of cardiodepressant autoantibodies and simplified method for screening such antibodies
(a) Patients and Methods
(i) Subject Patients The study was conducted on 104 patients who were diagnosed with dilated cardiomyopathy (DCM) based on the criteria from the World Health Organization/International Society and Federation of Cardiology (Richardson P, McKenna W, Bristow M R et al., Circulation (1996) 93:841-2). At the time of sample acquisition, all patients were stable under conventional therapy, including digitalis, diuretics, angiotensin-converting enzyme inhibitors, or β blockers. A left ventricular ejection fraction (LVEF) <45% was confirmed by radionuclide ventriculography. Coronary angiography was performed on 98 patients, and endomyocardial biopsy was performed on 87 patients. In all 87 samples, hematoxylin-eosin staining was able to exclude the presence of secondary myocardial diseases; and notably, the absence of chronic myocarditis was confirmed in all samples. Hypertrophy of cardiac muscle cells was found in 72 patients (83%), and significant interstitial fibrosis was found in 63 patients (72%). However, immunohistochemistry (IHC) for specific antigens or lymphocytes was not performed. Patients with >75% stenosis of the major coronary arteries were also excluded. The present inventors' study complied with the Declaration of Helsinki. The study protocol was approved by an institutional Review Committee, and all patients gave written informed consent to participate in the study.
(ii) Antibody Detection The antibodies of interest were measured in the patient sera with an enzyme-linked immunosorbent assay (ELISA), immunoblotting, or standard indirect immunofluorescence (i.e. IHC). Antigens purchased for ELISA were purified proteins such as Na—K-ATPase (Sigma Chemical, St. Louis, Mo., USA), cardiac troponin I (Wako Pure Chemical, Osaka, Japan), and synthetic peptides corresponding to the putative sequence of the second extracellular loop of human G protein-coupled receptors such as β1- and M2-receptors. For ELISA to detect such antibodies, 96-well ELISA plates (Iwaki Glass, Chiba, Japan) coated with 50 μL of 50 mg/L antigen dissolved in 0.1 M carbonate-bicarbonate buffer (pH 9.6) plus 0.5% gelatin were used. Blocking was performed by phosphate buffered saline (PBS: 10 mmol/L phosphate, 140 mmol/L NaCl, pH 7.4) supplemented with 3% bovine serum albumin and 0.1% Tween-20 (Wako Pure Chemical). After blocking, 50 μl of patient serum or purified immunoglobulin G (IgG) dilutions beginning at 1:20 were then added to the coated and saturated microtiter plates. After the wells were washed three times, a peroxidase-conjugated goat anti-human IgG (H+L) antibody (1:1000 dilution; Biosource, Camarillo, Calif., USA) was added and allowed to react for one hour. After washing, the bound peroxidase-conjugated antibody was detected by incubating the plates for one hour with orthophenylenediamine dihydrochloride (Organon Teknika, West Chester, Pa., USA). A solution of 2.5M sulfuric acid was added to stop the reaction and the optical density was read at 492 nm in a microtiter reader, with a positive finding defined as an optical density that was 2.5 times the background density.

(iii) Ex Vivo Assay of Cardiodepressant Antibodies

Figure 1:
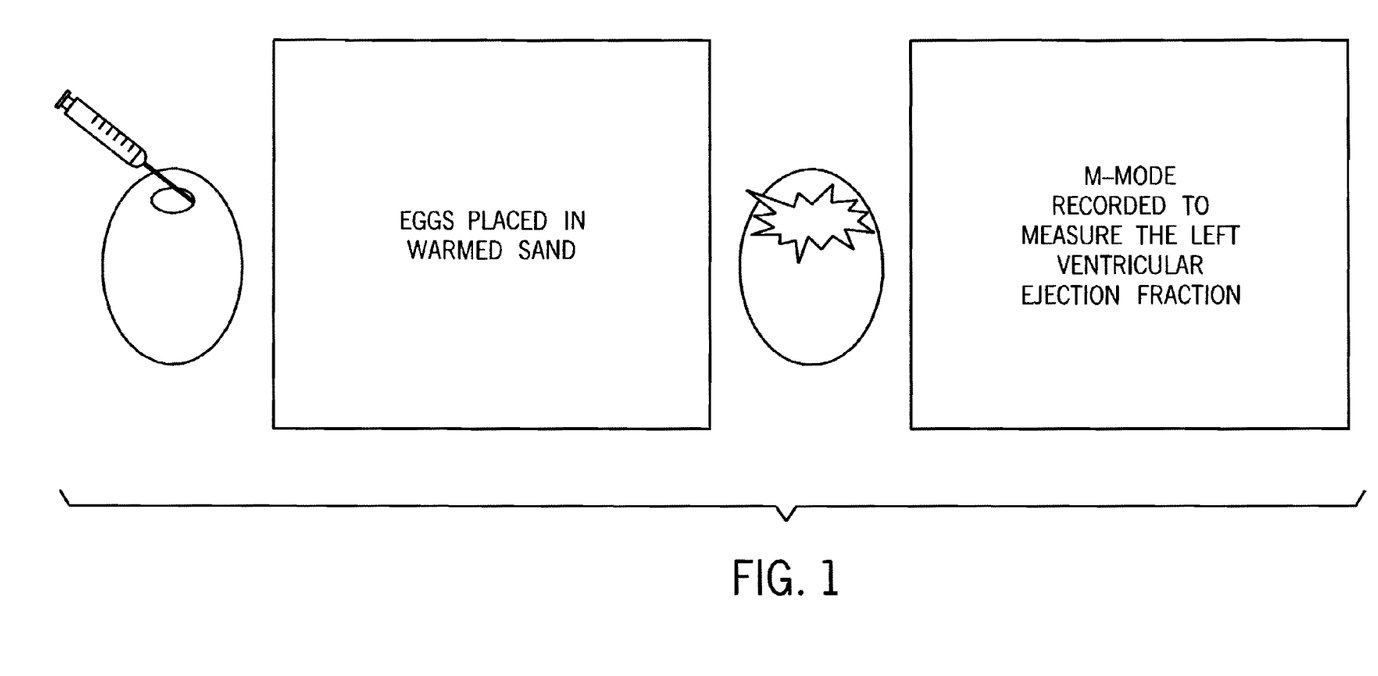

Ultrasonic echocardiography (UCG) was performed on chick embryos in order to determine the effects of antibodies on cardiac function (FIG. 1). As previously described (Sugiyama T, et al., Toxicol Appl Pharmacol (1996) 138:262-7), fertile White Leghorn chicken eggs (Ohmiya Poultry Laboratory, Saitama, Japan) were incubated at 37.5±0.2° C. at a relative humidity of about 65%, and turned automatically every hour (P-1 type; Showa Incubator Laboratory, Omiya, Japan). IgG was purified by protein G-agarose methods. On the 18th day, purified patient IgG was added to the oval air sac (1.0 mg/egg) ten minutes after the injection of an anesthetic agent. After 20 minutes, UCG was performed by inserting the echo probe through the small hole created around the air sac part. Left ventricular end-diastolic and end-systolic dimensions, LVEF and the RR interval were determined by repeated M-mode measurements (at least three measurements were made). A portable incubator was used to keep the temperature at 37.5° C. until the start of UCG, and the eggs were always placed on warmed sand in order to maintain the chicks' respiration and the temperature during the examination. The mean±2 SD of the LVEF in the presence of physiological saline was determined (N=10), and a positive outcome for cardiodepressant antibody was defined to be when the LVEF was lower than the mean−2SD in the presence of IgG purified from patients with DCM and those with heart failure of specific etiology (non-DCM; N=10). All non-DCM patients were old myocardial infarction patients, and their age, gender, and LVEF values were matched to those of the DCM patients (age: 56±10 years; 8 females; LVEF: 32±11%). It has been shown that the IgG fraction was not contaminated with cytokines and neurohormones, including interleukin-6, tumor necrosis factor-α, norepinephrine, or natriuretic peptides.

(iv) Clinical Features of Antibody-Positive Patients

Patients with and without cardiodepressant antibodies were compared in terms of age, gender, New York Heart Association (NYHA) functional class, LVEF, left ventricular dimensions, plasma norepinephrine and atrial natriuretic peptide concentrations, the number of premature ventricular contractions, and the presence of ventricular tachycardia (VT) on 24-hour electrocardiographic Holter monitoring. The clinical variables and the parameters measured by UCG and Holter electrocardiographic monitoring were collected within one month after serum sampling to determine cardiac antibodies. UCG was performed using a commercially available probe and system. The Holter electrocardiogram was analyzed on two standard channels by using the Marquette system (SXP 8000 or MARS 8000) to assess the basal heart rhythm, total number of supraventricular and ventricular premature contractions, and the presence of VT (defined as three or more consecutive premature ventricular contractions with a heart rate >100 beats/min), which was noted in at least one of the tests. Data were averaged from two or more sets of recordings.

(v) LVEF Before and After Removal of Antibodies

The effects of removal of such antibodies on cardiac function were determined by measuring the LVEF of the chick embryos using UCG. All patient sera were incubated with a tryptophan column (Asahikasei Medical, Tokyo, Japan) to deplete antibodies. Five hundred microliters of patient serum was incubated with an equal volume of this column material at 37° C. for 2 hours. The LVEF in the presence of crude patient serum (100 μl/egg) was compared with that in the presence of patient serum after antibody depletion. Not only DCM patient samples (N=42), but also non-DCM patients samples (N=12) were evaluated by this method. All DCM patients had β1- and/or M2-receptor antibodies, but no non-DCM patients had such antibodies. It has been shown that this depletion procedure did not influence any drug or humoral factor concentration except for IgG.

(vi) Statistical Analysis

The data were expressed as mean±SD. Comparison between the two groups was performed using the non-paired t-test. The difference in the antibody-positive rate was assessed using the $\chi^2$-test. Multivariate analysis was performed to determine the significance of various antibodies in predicting the presence of cardiodepressant antibodies. Statistical significance was set at $P<0.05$.

(b) Results

Figure 2:
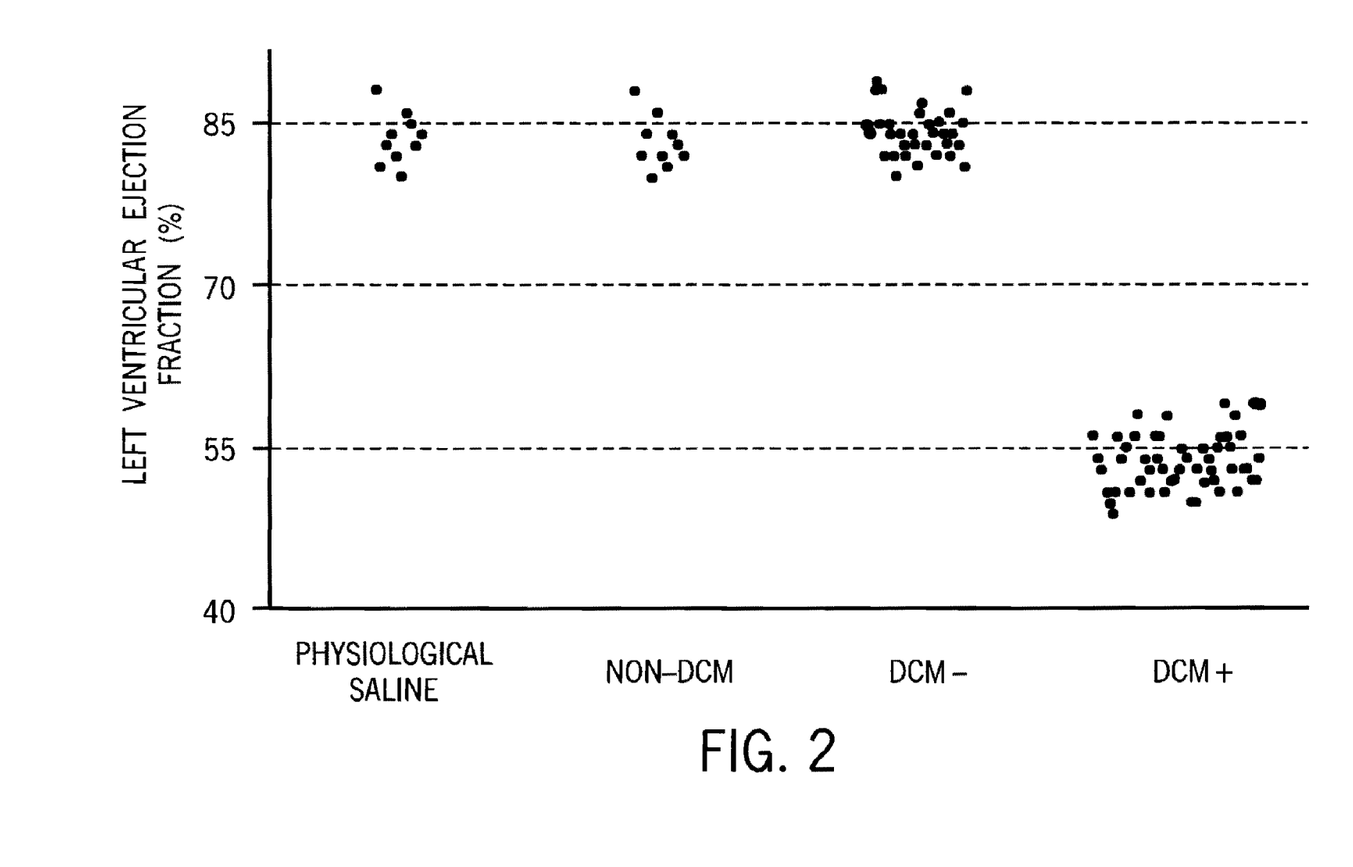

The LVEF measured by UCG in chick embryo hearts in the presence of saline was 83.6±2.3%. The LVEF in the presence of IgG purified from patients with non-DCM was 83.2±5.7%. Cardiodepressant antibodies were found to be negative in 39 patients with DCM, in whom the LVEF was 84.0±4.3%. There was no significant difference in the LVEF of these three groups. In contrast, cardiodepressant antibodies were found to be positive in 65 patients with DCM, with the LVEF being 53.5±5.1%, which was significantly lower than that obtained in the presence of non-cardiodepressant antibodies ($P<0.0001$, FIG. 2). Table 1 shows the clinical profiles of patients with and without cardiodepressant antibodies.

TABLE 1

|  | Cardiodepressant antibodies (+) | Cardiodepressant antibodies (−) |
|---|---|---|
| Number of patients (%) | 65 (63%) | 39 (37%) |
| Age | 58 ± 13 | 53 ± 15 |
| Gender (male/female) | 50/15 | 31/8 |
| NYHA class (I/II/III + IV) | 34/24/7 | 19/14/6 |
| LVEF (%) | 31 ± 9 | 30 ± 10 |
| EDD (mm) | 60 ± 10 | 62 ± 11 |
| LA (mm) | 40 ± 8 | 42 ± 7 |
| Persistent AF (%) | 21 (32) | 11 (28) |
| NSVT (%) | 27 (42) | 21 (54) |

TABLE 1-continued

|  | Cardiodepressant antibodies (+) | Cardiodepressant antibodies (−) |
|---|---|---|
| PNE (pg/mL) | 412 ± 301 | 438 ± 275 |
| ANP (pg/mL) | 89 ± 95 | 84 ± 67 |

The abbreviations used in the above Table are as follows: AF, atrial fibrillation; ANP, atrial natriuretic peptide; EDD, left ventricular end-diastolic dimension; LA, left atrial dimension; LVEF, left ventricular ejection fraction measured by radionuclide ventriculography; NSVT, non-sustained ventricular tachycardia; NYHA, New York Heart Association; PNE, plasma norepinephrine concentration.

There was no difference in age, gender, NHYA functional class, LVEF measured by radionuclide ventriculography, left ventricular end-diastolic dimensions, left atrial dimension, plasma atrial natriuretic peptide and norepinephrine levels, and the incidence of arrhythmias including atrial fibrillation and non-sustained VT, between the two groups.

Figure 3:
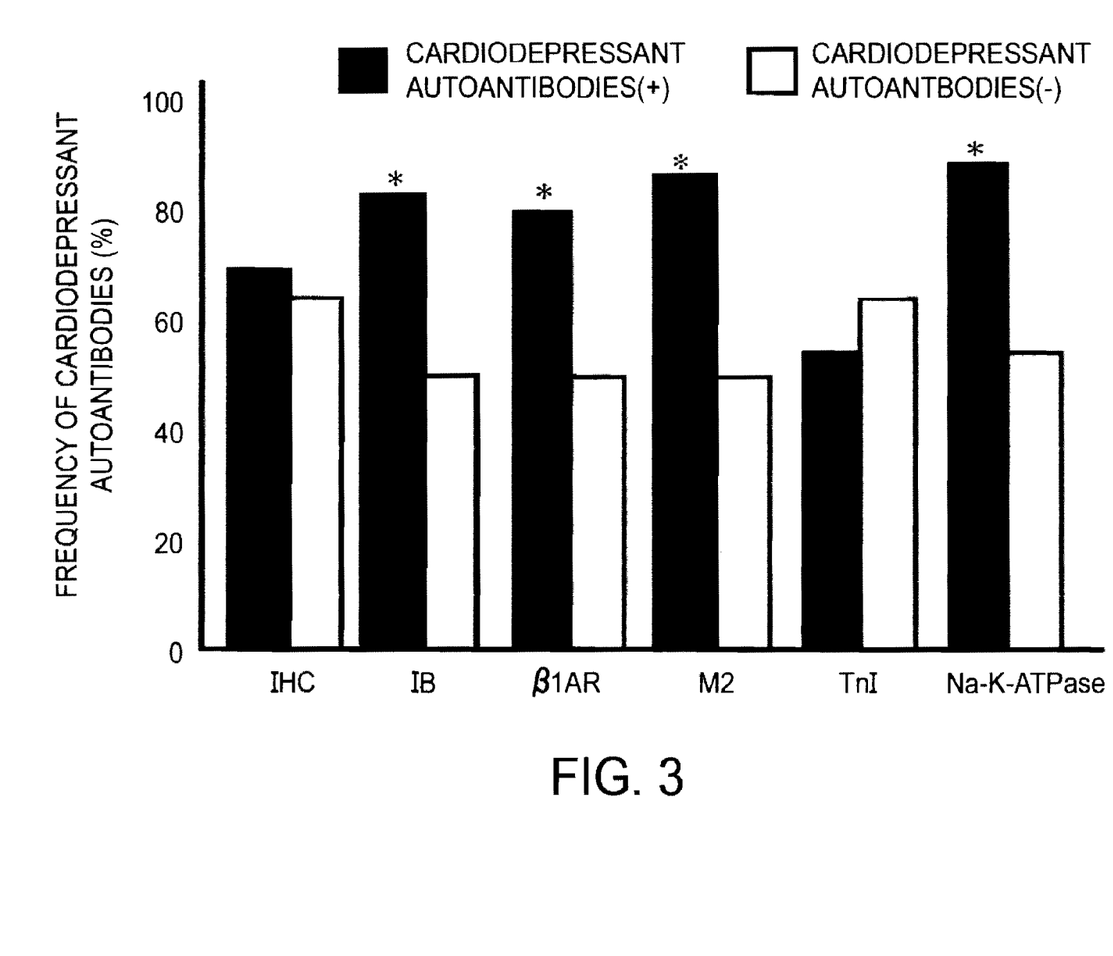
FIG. 3 shows the frequency (%) of cardiodepressant autoantibodies, as determined by the presence or absence of specific antibodies. Cardiodepressant antibodies were more common in patients who exhibited immunoblot (IB)-positive antibodies or who were ELISA-positive for β1-adrenergic receptors (β1AR), muscarinic M2-acetylcholine receptors (M2), and Na—K-ATPase, than those without such autoantibodies. *$P<0.01$ autoantibody-positive vs. autoantibody-negative patients. IHC, immunohistochemistry; TnI, troponin I.

Correlation of the cardiodepressant antibodies with other antibodies determined by IHC, immunoblotting, and specific antibodies determined by ELISA including those directed against β1 receptors, M2 receptors, Na—K-ATPase, and cardiac troponin I, was examined (FIG. 3). Cardiodepressant antibodies were found in 25 out of 39 patients who were positive for immunohistocliemically determined antibodies. In contrast, cardiodepressant antibodies were found in 40 out of 65 patients who were negative for immunohistochemically determined antibodies. There was no difference in the incidence of cardiodepressant antibodies between the two groups (64.1% vs. 61.5%, NS). Cardiodepressant antibodies were more commonly found in patients who were positive for antibodies determined by immunoblotting than those who were negative for such antibodies (81.6% vs. 51.5%, P<0.05). For autoantibodies determined by ELISA, cardiodepressant antibodies were more commonly found in patients with antibodies directed against β1-receptors than those without antibodies (81.0% vs. 51.6%, P<0.05). Cardiodepressant antibodies were also more common in patients with antibodies directed against M2-receptors (83.3% vs. 48.4%, P<0.05) and Na—K-ATPase (84.6% vs. 55.1%, P<0.05). Cardiodepressant antibodies were similarly found between patients who were positive and those who were negative for antibodies directed against troponin I (56.3% vs. 63.6%, NS).

Next, the significance of antibodies determined by immunoblotting, and antibodies assessed by ELISA for β1 receptors, M2 receptors, and Na—K-ATPase, in predicting the presence of cardiodepressant antibodies was evaluated using multivariate analysis. Antibodies directed against β1- and M2-receptors were significant in predicting the presence of cardiodepressant antibodies. By contrast, antibodies determined by immunoblotting and those directed against Na—K-ATPase were not significant as predictors (Table 2).

TABLE 2

|  | Odds ratio | 95% CI | P-value |
|---|---|---|---|
| Immunoblotting (+) | 3.1 | 0.8-11.9 | 0.09 |
| Antibodies for β1AR (+) | 10.6 | 3.4-33.1 | <0.01 |
| Antibodies for M2 (+) | 13.8 | 4.3-43.8 | <0.01 |
| Antibodies for Na-K-ATPase (+) | 1.8 | 0.4-8.3 | 0.45 |

The abbreviations used in the above Table are as follows: β1AR, β1 adrenergic receptor; M2, muscarinic M2 acetylcholine receptor.

Figure 4:
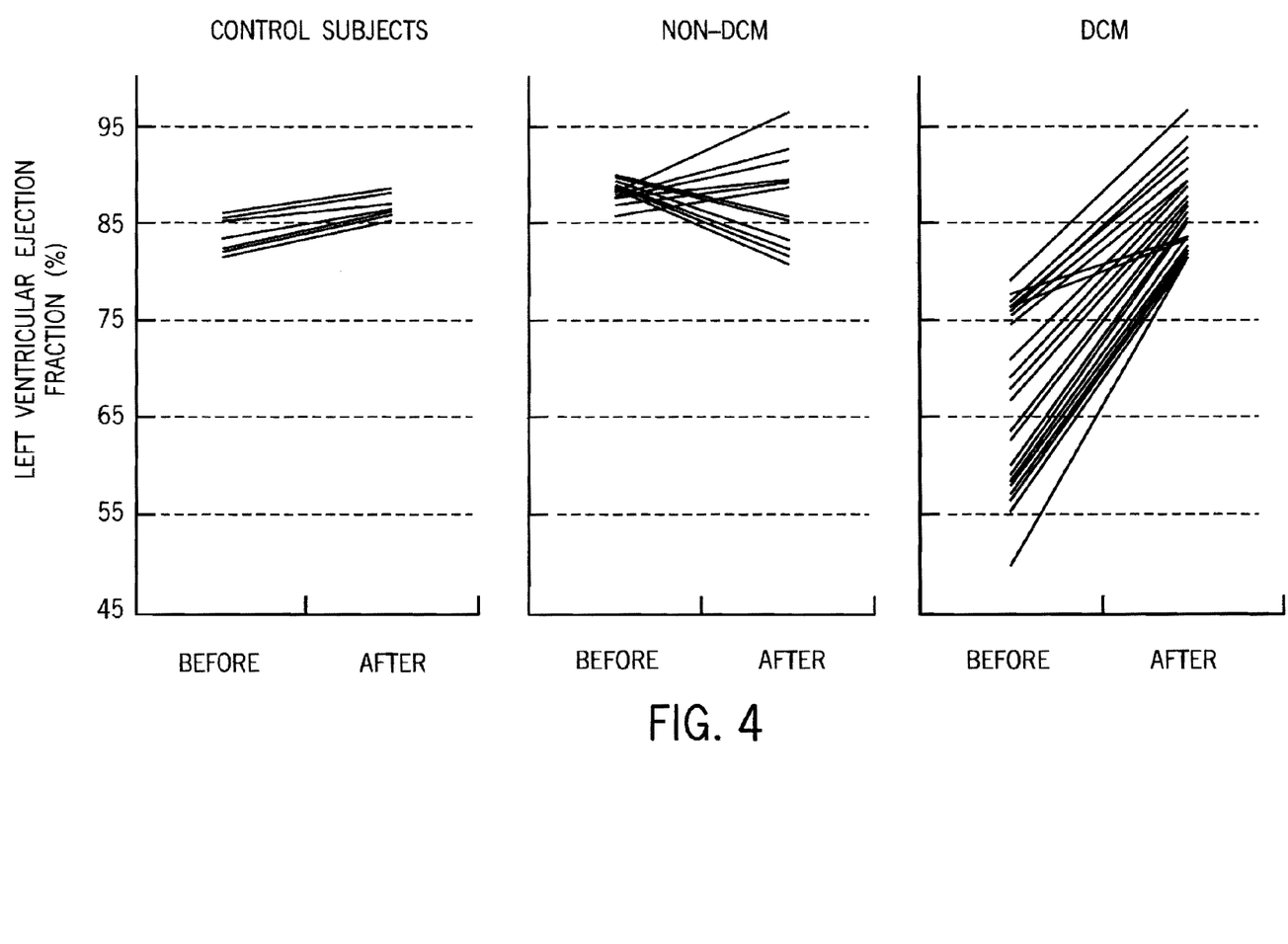
FIG. 4 shows the effects of autoantibody depletion of patient serum by tryptophan-containing gel. Cardiac function was compared before and after autoantibody depletion by tryptophan-containing gel. Cardiac function was not altered after autoantibody depletion in the presence of serum from control subjects (N=10) or from patients with non-DCM heart failure (N=12). However, cardiac function was increased by the depletion procedure in the presence of serum from patients with DCM who were positive for the cardiodepressant autoantibodies (N=43).

The LVEF was significantly higher in the presence of serum after antibody depletion than in the presence of crude serum for patients with DCM who were positive for cardiodepressant antibodies (86.3±3.4% vs. 65.5±7.8%, P<0.01; FIG. 4). The LVEF remained unchanged before and after antibody depletion for patients with non-DCM. LVEF was higher in the presence of serum after antibody depletion than in the presence of crude serum from patients who were positive for antibodies directed against β1-receptors (86.2±3.5% vs. 65.6±8.4%; P<0.01; N=26) and those directed against M2-receptors (86.0±3.1% vs. 7.8%; P<0.01; N=20). There were four patients who were positive for antibodies directed against both β1- and M2-receptors. The LVEF was similarly improved after antibodies were depleted by the tryptophan-containing gel.

Example 2

Figure 51:
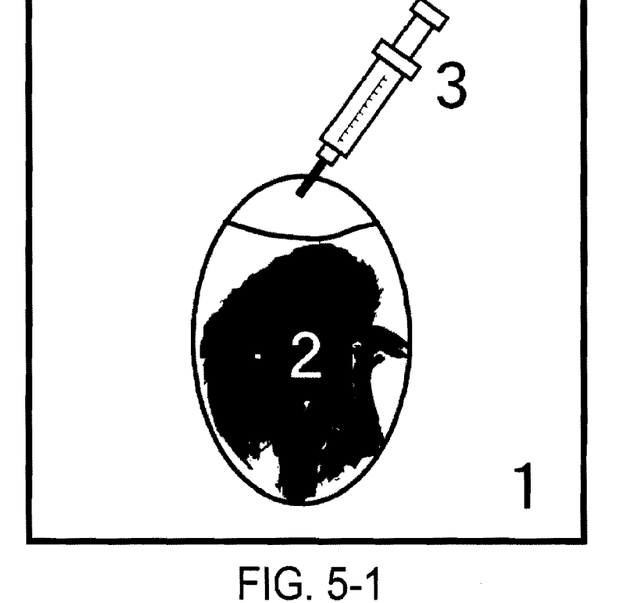
Figure 52:
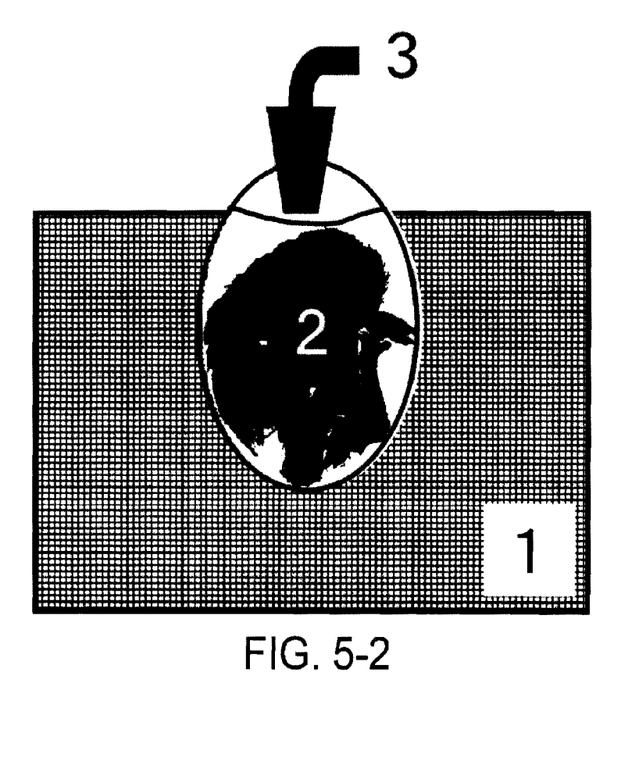
Figure 53:
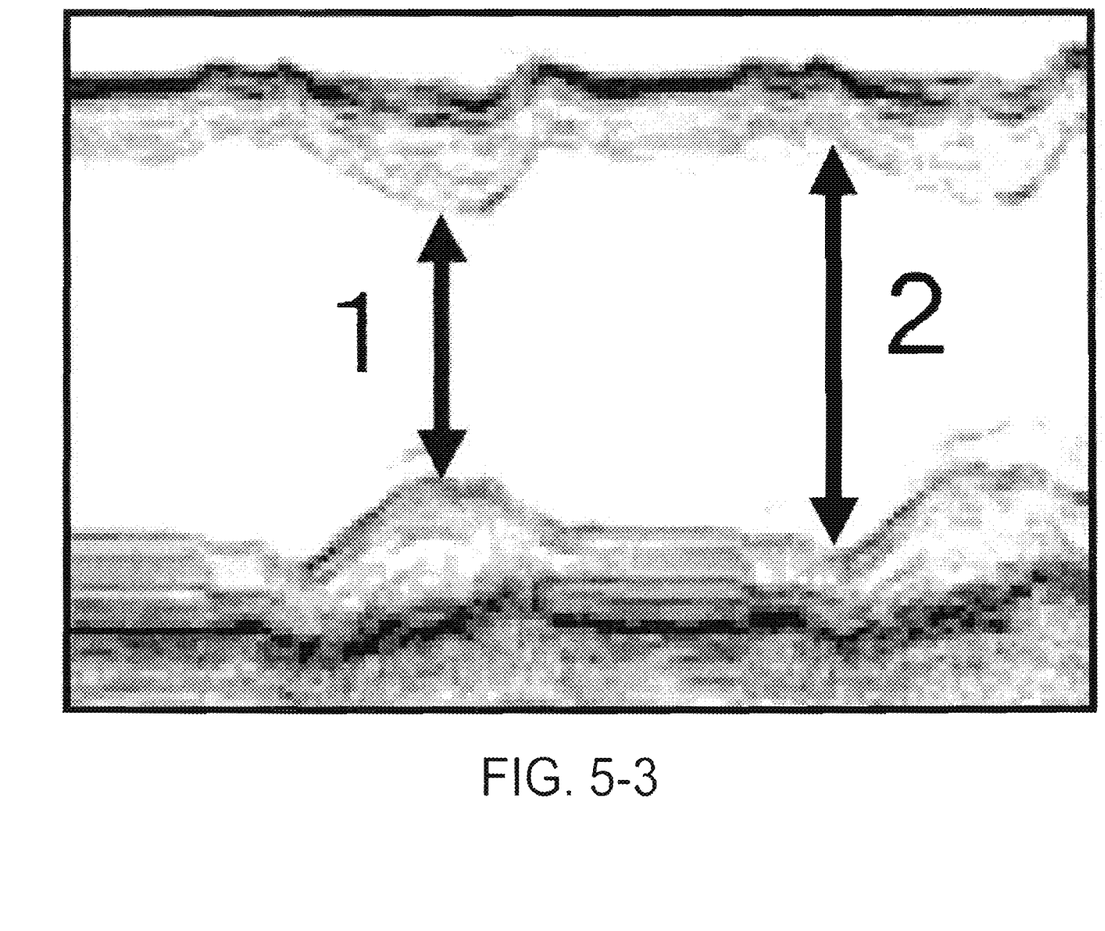

Method for Predicting the Effectiveness of Apheresis Therapy (a) Experimental Procedures Chicken fertile eggs used were stored in an incubator at 37.8° C. until immediately before experiment. Eggs with a heart rate of 300 beats/min or less were not used. First, a small hole with a diameter of 1 to 2 mm was created on the eggshell using an electric grinder, and an anesthetic agent (a mixed solution of 45 mg of urethane and 4.5 mg of alpha-chloralose) was added through the hole. After ten minutes, 200 μl of patient serum was added through the hole (FIG. 5-1). After 20 minutes, the hole was enlarged to a diameter of 20 to 30 mm using forceps, and immediately the eggs were placed in incubation sand at 40° C. (FIG. 5-2). Warmed jelly was added into the air sac, and M-mode echocardiographic images of the chick heart were obtained using an ultrasonic probe (FIG. 5-3). The "left ventricular ejection fraction (LVEF)" calculated from the left ventricular end-systolic and end-diastolic dimensions was recorded. At least two or more negative controls (200 μl of physiological saline) were used in each measurement carried out by two or more experimenters. Persons adding anesthetic/samples and persons recording echocardiograms were both double-blinded to the details of each sample. The experiment confirmed that (1) the measured value for every negative control group was 90%, and (2) the standard deviation of the measured value for the negative control group was less than 5%. When the chicken LVEF in the presence of a patient sample was less than 90%, the measurement result was determined to be "positive".

(b) Results (1) The therapeutic outcome of 17 dilated cardiomyopathy patients in Japan who had received apheresis therapy by May 2008 were evaluated after three months of therapy (by August 2008). Ten cases were "positive" in the measurement prior to treatment, while eight cases were "negative" in the measurement after treatment (completely cured group). The remaining nine cases were designated as incompletely cured group. These two groups were compared.

(2) After three months of treatment, LVEF was improved from 20±8% to 29±9% in the completely cured group. In contrast, the incompletely cured group showed no difference (from 18±10% to 17±7%). Thus, there was a significant difference between the two groups (p<0.001; repeated measure ANOVA).

(3) There was one case which was once categorized into the incompletely cured group after three cycles of apheresis therapy (first course), but was later placed in the completely cured group after receiving five cycles of apheresis therapy three months later (second course). The patient's LVEF was unchanged (from 22% to 22%) three months after the first course, but increased from 22% to 37% three months after the second course. It was thus demonstrated that the present invention enabled determination of appropriate timing and cycles of apheresis therapy.

(4) In the present invention, the cost necessary is less than 600 yen/sample, and time required for the measurement (anesthesia, sample administration, and measurement) was 30 minutes/sample. In the negative control experiment using physiological saline, the standard deviation of LVEF of chicken fertile eggs was as small as 2.3% among ten samples, demonstrating high reproducibility. Thus, the present invention was shown to be superior in all aspects to the methods using cultured cells as attempted in the U.S. and Europe.

(5) The type and dose of anesthetic agent, which are important experimental conditions in the present invention, have been disclosed for the first time as described above. While LVEF of chicken fertile eggs cannot be measured without suppressing the body movement, the proper setting of anesthetic conditions was indispensable since the heart rate and function vary depending on the conditions. Stable measurement was impossible with conventional anesthetics (pentobarbital, Nembutal, thiopental, ketamine, xylazine, diazepam, and propofol).

(6) The temperature of incubation sand, which is an important experimental condition in the present invention, has also been disclosed for the first time as described above. Although blood vessels and blood flow have reportedly been observed in incubation sand at 37 to 38° C., such temperatures are inappropriate in the measurement of LVEF. This is because the temperature of the chick in the egg becomes lower than the temperature around the egg and results in measurement errors caused by a negative inotropic effect produced upon the addition of heterologous serum (patient serum). When the temperature was 40° C. as described above, the standard deviation of LVEF was 4.2% in the measurement of ten negative samples.

INDUSTRIAL APPLICABILITY

Autoimmunity, as well as viral infection and genetic predisposition, have been suggested as causes of dilated cardiomyopathy (DCM). Among them, some cardio-specific autoantibodies play a role in the pathophysiology of congestive heart failure. Antibodies directed against the second extracellular loop of β1 adrenaline (β1) receptors are well known and are found in approximately 40% of patients with DCM. The present inventors have shown, as have other research groups, that persistent production of these antibodies induces cardiac dysfunction associated with hypertrophy and β-adrenergic receptor uncoupling, as well as electrical instability with altered expression of cardiac ion channels. The presence of antibodies directed against muscarinic M2-acetylcholine (M2-) receptors was associated with persistent atrial fibrillation, and actually induced supraventricular arrhythimias in chick embryo hearts. The present inventors found that antibodies directed against the catalytic α-subunit of sarcolemmal Na—K-ATPase were found in certain patients with DCM. The antibodies inhibited Na—K-ATPase activity and their presence predicted sudden cardiac death associated ventricular tachycardia (VT) in patients with DCM. In addition, antibodies directed against cardiac troponin I was found in sera from programmed cell death-1 immunoregulatory receptor-deficient mice that exhibited DCM. Administration of monoclonal antibodies to cardiac troponin I induced cardiac dilation and dysfunction, and augmented the L-type calcium current.

Immunoadsorption (IA) to remove such antibodies may be an effective tool in treating refractory heart failure due to DCM. However, it is essential to establish how to identify patients who would benefit from such an expensive therapy, since the antibody profile is complex in patients with DCM. Recently, Staudt et al. reported that the presence of "cardiodepressant antibodies", defined as both a decrease in calcium transient and cell shortening in adult rat ventricular myocytes, was associated with improved cardiac function (Staudt A, Staudt Y, Dörr M et al., J Am Coll Cardiol 2004; 44:829-36). The present inventors attempted to establish a more convenient screening system to identify such cardiodepressant antibodies in sera from patients with DCM.

The present invention has identified cardiodepressant antibodies that could directly influence left ventricular ejection fraction (LVEF) in patients with dilated cardiomyopathy (DCM), and established a simple screening method for these antibodies. Not only acute hemodynamic but also chronic prognosis improvements were reported with immunoadsorption in some patients with DCM. Various antibodies determined by immunohistochemistry, immunoblotting, and enzyme-linked immunosorbent assay (β1-adrenergic [β1-] receptors, muscarinic M2-acetylcholine [M2-] receptors, troponin I, or Na—K-ATPase) were measured in 104 patients with DCM. Cardiodepressant antibodies were also determined by ultrasonic echocardiography (UCG) of 18 day old chick embryos after adding the patients' purified immunoglobulin G, and the following clinical features were compared: age, gender, New York Heart Association class, LVEF, neurohumoral factors, arrhythmias, and other antibodies. The in vitro immunoadsorption effect against these cardiodepressant antibodies was also examined. Cardiodepressant antibodies were found in 63% of 104 patients with DCM and had no relation to other clinical parameters, except for some antibodies such as anti-β1-receptor antibodies (81% vs. 52%, P<0.01), anti-M2-receptor antibodies (83% vs. 48%, P<0.01), or anti-Na—K-ATPase antibodies (85% vs. 55%, P<0.01). However, cardiodepressant antibodies were similarly found in patients with and without antibodies against troponin I (56% vs. 64%). The LVEF of chick embryos measured by UCG in the presence of patient serum was improved after in vitro immunoadsorption. The ex vivo system using chick embryos was able to determine cardiodepressant antibodies. Multivariate analysis revealed that antibodies against β1- or M2-receptors were predictors of these autoantibodies.

The invention claimed is:

1. A method for predicting an effectiveness of apheresis therapy on a patient with dilated cardiomyopathy, comprising the steps of:
   (a) adding a test sample obtained from said patient to a chicken fertile egg;
   (b) measuring left ventricular ejection fraction (LVEF) of said chicken fertile egg; and
   (c) predicting that apheresis therapy may be effective for the patient when said LVEF is reduced by the addition of said test sample.

2. The method of claim 1, wherein the test sample is serum, plasma, or purified immunoglobulin.

3. The method of claim 1, wherein the chicken fertile egg is 18 days old.

4. The method of claim 1, wherein the chicken fertile egg is incubated at 40° C. during the measuring in step (b).

5. The method of claim 1, wherein LVEF is measured by ultrasonic echocardiography.

6. The method of claim 5, wherein ultrasonic probe frequency is 10 MHz or higher in step (b).

7. The method of claim 1, which further comprises the step of administering an anesthetic agent to the chicken fertile egg before step (b).

8. The method of claim 7, wherein the anesthetic agent is urethane.

* * * * *

UNITED STATES PATENT AND TRADEMARK OFFICE
CERTIFICATE OF CORRECTION

PATENT NO.        : 8,106,012 B2
APPLICATION NO.   : 12/413968
DATED             : January 31, 2012
INVENTOR(S)       : Akiyasu Baba It is certified that error appears in the above-identified patent and that said Letters Patent is hereby corrected as shown below:

Column 8, line 3:

Delete "(86.0±3.1% vs. 7.8%;" and substitute therefor "(86.0±3.1% vs. 65.7±7.8%;".

Signed and Sealed this
Twenty-fifth Day of September, 2012

David J. Kappos
*Director of the United States Patent and Trademark Office*